(12) United States Patent
Rold et al.

(10) Patent No.: US 8,025,622 B2
(45) Date of Patent: Sep. 27, 2011

(54) SYSTEMS AND METHODS FOR ESTIMATING THE SIZE AND POSITION OF A MEDICAL DEVICE TO BE APPLIED WITHIN A PATIENT

(75) Inventors: Michael D. Rold, Modesto, CA (US); Shashidhar Sathyanarayana, Pleasanton, CA (US); Tat-Jin Teo, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1030 days.

(21) Appl. No.: 11/865,699

(22) Filed: Oct. 1, 2007

(65) Prior Publication Data

US 2008/0051657 A1 Feb. 28, 2008

Related U.S. Application Data

(63) Continuation-in-part of application No. 11/069,206, filed on Feb. 28, 2005, now Pat. No. 7,892,177.

(51) Int. Cl.
*A61B 8/12* (2006.01)
(52) U.S. Cl. ........................ 600/463; 600/437
(58) Field of Classification Search .................. 600/424, 600/425, 427, 437, 463; 715/769, 810
See application file for complete search history.

(56) References Cited

U.S. PATENT DOCUMENTS

| | | | |
|---|---|---|---|
| 4,841,977 A | 6/1989 | Griffith et al. |
| 5,000,185 A | 3/1991 | Yock |
| 5,117,831 A | 6/1992 | Jang et al. |
| 5,203,338 A | 4/1993 | Jang |
| 5,321,501 A | 6/1994 | Swanson et al. |
| 5,368,035 A | 11/1994 | Hamm et al. |

(Continued)

FOREIGN PATENT DOCUMENTS

WO WO-0041626 7/2000

(Continued)

OTHER PUBLICATIONS

Wenguang, L. et al: "Semiautomatic Frame-To-Frame Tracking of the Luminal Border From Intravascular Ultrasound," Proceedings of the computers in Cardiology Meeting, Venice, Sep. 23-26, 1991, New York, vol. Meeting 18, Sep. 23, 1991.

(Continued)

*Primary Examiner* — Tse Chen
*Assistant Examiner* — Peter Luong
(74) *Attorney, Agent, or Firm* — Frommer Lawrence & Haug LLP; Patrick R. Turner

(57) ABSTRACT

The field of the invention relates to medical imaging systems, and more particularly to systems and methods for estimating the size and position of a stent or other medical device within a patient. In one embodiment, a medical imaging system includes an elongated tubular member having distal and proximal ends, configured to be inserted into a vessel of a patient, an imaging device coupled to the distal end of the elongated tubular member, and a console electrically coupled to the imaging device, wherein the console includes a computer-usable medium, electrically coupled to the imaging device, having a sequence of instructions which, when executed by a processor, causes said processor to execute a process including generating an image of the vessel, and overlay one or more shapes onto the image to provide a visual approximation of the size and position of a medical device to be applied within the patient.

29 Claims, 6 Drawing Sheets

U.S. PATENT DOCUMENTS

| | | | |
|---|---|---|---|
| 5,538,003 | A | 7/1996 | Gadonniex et al. |
| 5,724,977 | A | 3/1998 | Yock et al. |
| 5,749,848 | A | 5/1998 | Jang et al. |
| 5,830,145 | A | 11/1998 | Tenhoff |
| 6,117,104 | A | 9/2000 | Fitz |
| 6,139,544 | A | 10/2000 | Mikus et al. |
| 6,193,657 | B1 | 2/2001 | Drapkin |
| 6,216,029 | B1 | 4/2001 | Paltieli |
| 6,245,017 | B1 | 6/2001 | Hashimoto et al. |
| 6,308,715 | B1 | 10/2001 | Weissman et al. |
| 6,379,302 | B1 | 4/2002 | Kessman et al. |
| 6,381,350 | B1 | 4/2002 | Klingensmith et al. |
| 6,381,351 | B1 | 4/2002 | Powell |
| 6,475,151 | B2 | 11/2002 | Koger et al. |
| 6,485,422 | B1 | 11/2002 | Mikus et al. |
| 6,544,176 | B2 | 4/2003 | Mikus et al. |
| 6,553,386 | B1 | 4/2003 | Alabaster |
| 6,585,654 | B2 | 7/2003 | White et al. |
| 6,592,526 | B1 | 7/2003 | Lenker |
| 6,669,635 | B2 | 12/2003 | Kessman et al. |
| 6,689,156 | B1 | 2/2004 | Davidson et al. |
| 6,786,870 | B2 | 9/2004 | Miyaki et al. |
| 2004/0068429 | A1* | 4/2004 | MacDonald .................... 705/10 |
| 2005/0107688 | A1 | 5/2005 | Strommer |

FOREIGN PATENT DOCUMENTS

| | | |
|---|---|---|
| WO | WO-2004051579 | 6/2004 |

OTHER PUBLICATIONS

Huang et al, "Optical Coherence Tomography, Science," vol. 254, pp. 1178-1181, Nov. 22, 1991.

U.S. Appl. No. 11/069,206; Official Communication, mail date Oct. 30, 2007.

U.S. Appl. No. 11/069,206; Official Communication, mail date Dec. 9, 2008.

* cited by examiner

SYSTEMS AND METHODS FOR ESTIMATING THE SIZE AND POSITION OF A MEDICAL DEVICE TO BE APPLIED WITHIN A PATIENT

RELATED APPLICATION

This is a continuation-in-part of application Ser. No. 11/069,206, filed on Feb. 28, 2005 now U.S. Pat. No. 7,892,177.

FIELD OF THE INVENTION

The field of the invention relates to medical imaging systems, and more particularly to systems and methods for estimating the size and position of a medical device to be applied within a patient.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

FIG. 1 shows an example of an imaging transducer assembly 1 known in the art. The imaging transducer 1 is typically within the lumen 10 of a guidewire (partially shown), having an outer tubular wall member 5. To obtain an image of a blood vessel, the imaging transducer assembly 1 may be inserted into the vessel. The transducer assembly 1 may then rotate while simultaneously emitting energy pulses, e.g., ultrasound waves, at portions of the vessel from within the vessel and receiving echo or reflected signals.

Turning to FIG. 2, it is known in the art that an imaging console 20 having a display screen, a processor and associated graphics hardware (not shown) may be coupled with the imaging transducer assembly 1 to form a medical imaging system 30. The imaging console 20 processes the received echo signals from the imaging transducer assembly 1 and forms images of the area being imaged. To form the images, the imaging console 20 draws multiple lines, known as "radial lines", (not shown) on the display screen that each correspond to an angular position of the transducer assembly 1. The processor of the imaging console 20 assigns brightness values to pixels of the lines based on magnitude levels of the echo signals received from the transducer assembly 1 at the angular positions corresponding to the lines. A drawing that includes a large number of these radial lines results in an image such as an intravascular ultrasound (IVUS) image (not shown).

It is further known in the art to continually capture frames of IVUS images while gradually withdrawing the transducer or catheter within a vessel. The resulting stack of frames may be stored and manipulated by the processor, and from these frames, a longitudinal image of the vessel may be generated. In other words, a visualization of the vessel in a plane containing the long axis of the vessel may be rendered, which allows the clinician to assess blockage at different locations along the length of the vessel. For example, U.S. Pat. No. 5,830,145, issued to Tenhoff, the disclosure of which is incorporated herein by reference, describes a system and method for generating longitudinal images of a region of a blood vessel.

The resulting longitudinal image may be used to diagnose abnormalities, such as blockage, within the vessel. A typical treatment known in the art for such abnormalities is the use of one or more stents in the region(s) of interest. Often times, determining the proper size (length and diameter) and position of the stent(s) to be applied within the patient is a "trial and error" type process, which may increase procedure time and risk to the patient. Accordingly, an improved system and method for delivering one or more stents would be desirable.

SUMMARY OF THE INVENTION

The field of the invention relates to medical imaging systems, and more particularly to systems and methods for estimating the size and position of a medical device to be applied within a patient.

In one embodiment, a medical imaging system includes an elongated tubular member having distal and proximal ends, configured to be inserted into a vessel of a patient, an imaging device coupled to the distal end of the elongated tubular member and configured to emit one or more energy pulses and receive one or more echo signals, and a console electrically coupled to the imaging device, wherein the console includes a computer-usable medium, electrically coupled to the imaging device, having a sequence of instructions which, when executed by a processor, causes said processor to execute a process including generating an image of the vessel, and providing a graphical representation of a stent or other medical device to be overlaid onto the image. In an exemplary embodiment, different shapes, e.g., a rectangle, may be overlaid onto the image to provide a visual approximation of the size and position of a medical device to be applied within the patient.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
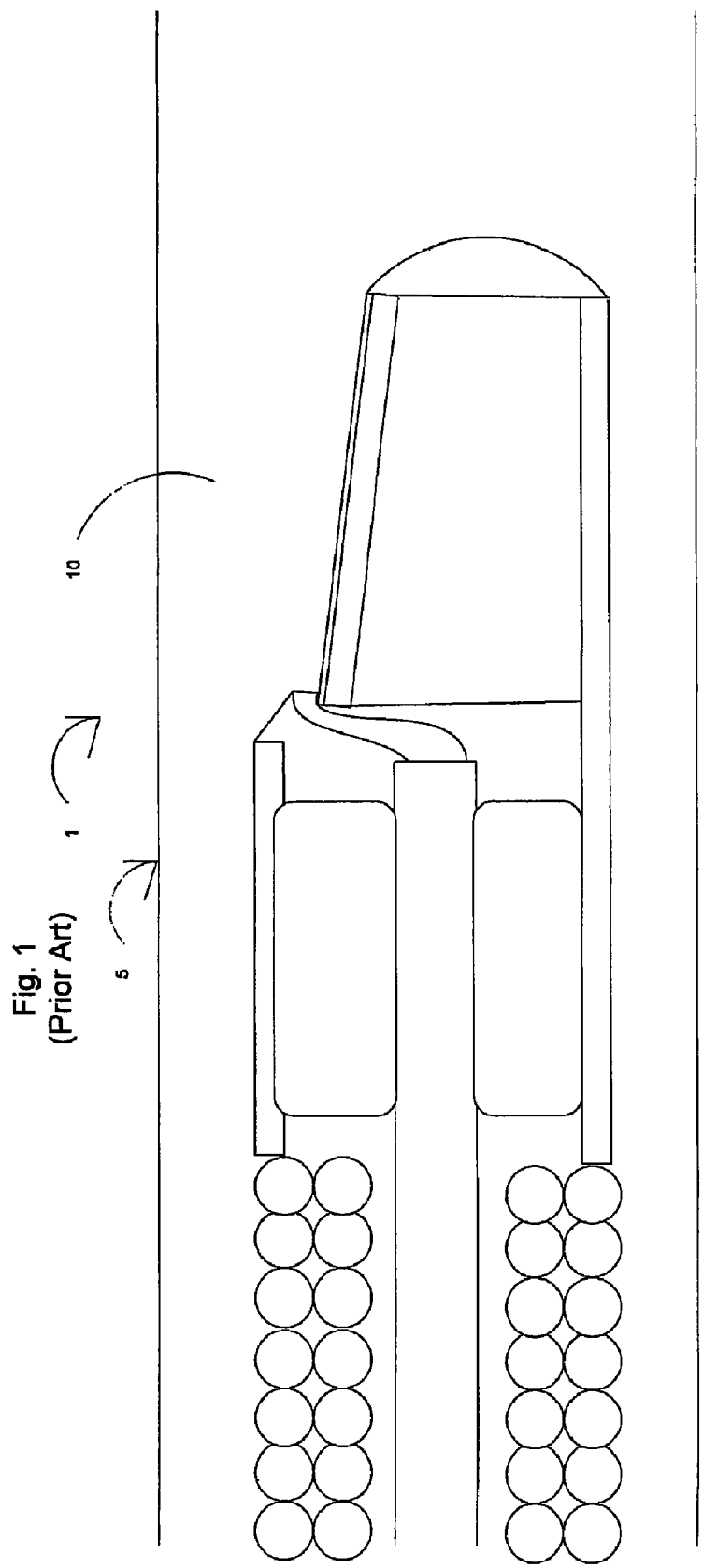
FIG. 1 is a cross-sectional side view of an imaging transducer assembly known in the art.
Figure 3:
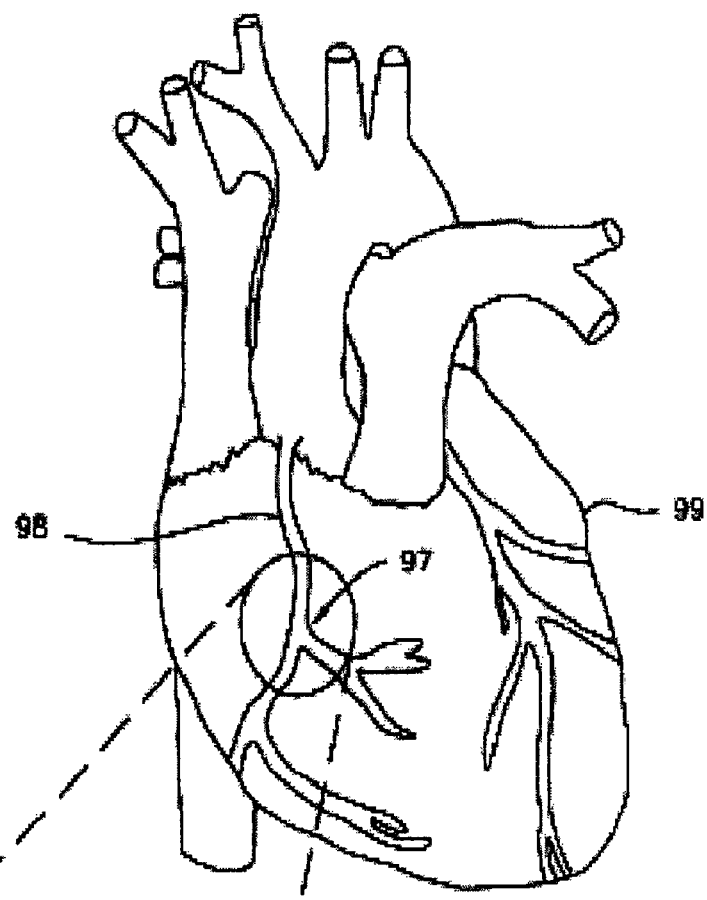
FIG. 3 depicts a human heart as a potential site for use of the method and apparatus disclosed herein.
Figure 4:
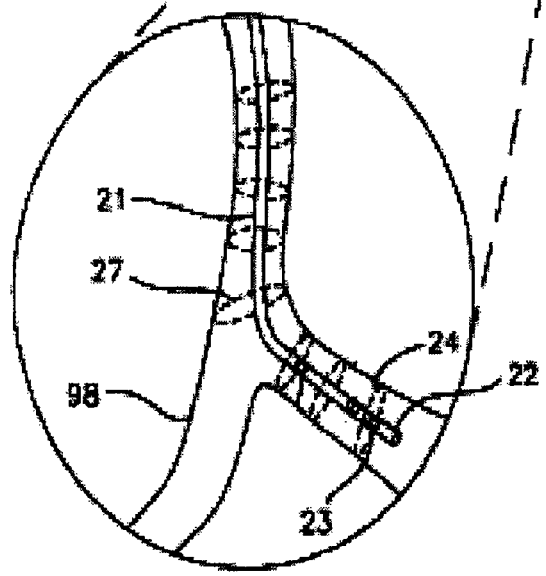
FIG. 4 depicts an exploded view of a region of the coronary arteries having an IVUS catheter positioned in a region of interest.

The methods and systems disclosed herein are applicable to medical imaging, such as ultrasound imaging, of vessels, such as the coronary arteries as depicted in FIG. 3, or to any body cavity where the image is to be obtained over a region. With reference to FIG. 3, heart 99 includes coronary arteries 98 which follow a tortuous path along the surface of the heart. FIG. 4 shows an exploded view of curvature 97, having an IVUS catheter 21 disposed within a region of interest therein. Catheter 21 has distal end 22 and a proximal end (not shown), and is generally designed in accordance with imaging catheters known in the art. The catheter thus includes an intraluminal ultrasound imaging system, such as that shown in FIG. 1., capable of obtaining echographic images of the surrounding of catheter tip 22. The imaging system includes transducer 23 and its associated electronics for displaying an echographic data set, e.g., obtained by scanning transducer 23 over a 360-degree path 24 about distal tip 22 of catheter 21, or by a sector scan which makes a 60 or 90 degree scan. In an alternative embodiment, transducer 23 is replaced by a phased array as disclosed in Griffith et al., U.S. Pat. No. 4,841,977. Further, other imaging devices may be used, instead of, or in addition to imaging transducers, such as light based apparatuses for obtaining images through optical coherence tomography (OCT). Image acquisition using OCT is described in Huang et al., "Optical Coherence Tomography," Science, 254, Nov. 22, 1991, pp 1178-1181. A type of OCT imaging device, called an optical coherence domain reflectometer (OCDR) is disclosed in Swanson U.S. Pat. No. 5,321,501, which is incorporated herein by reference. The OCDR is capable of electronically performing two- and three-dimensional image scans over an extended longitudinal or depth range with sharp focus and high resolution and sensitivity over the range.

Figure 5:
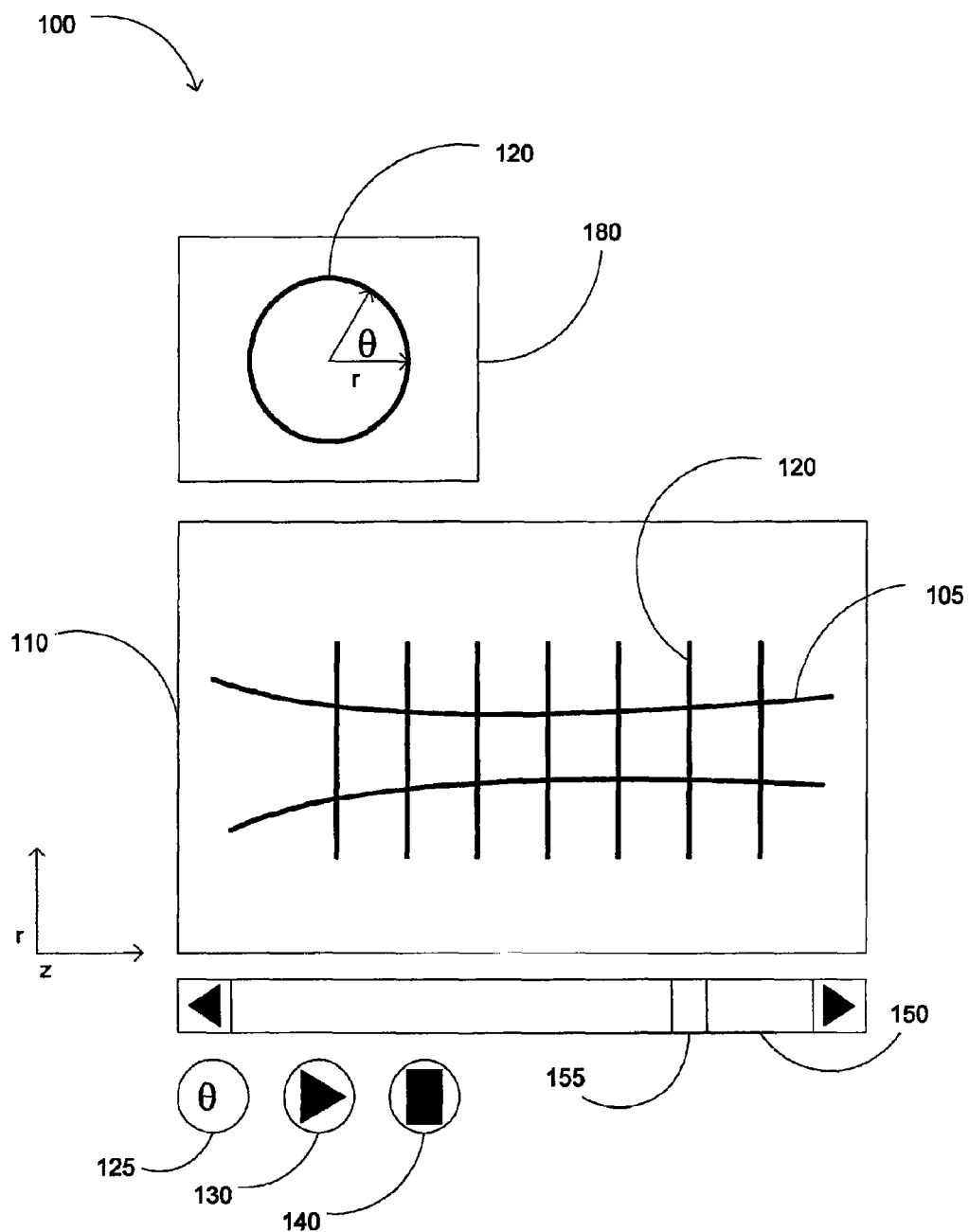
FIG. 5 depicts a user interface for displaying a longitudinal medical image known in the art.

Scanning of the vessel interior is repeated many times during pull-back to obtain a plurality of echographic data sets taken at a sequence of positions 27 within vessel 98. In one embodiment, each echographic data set obtained during pull-back comprises a transverse or cross-sectional (i.e., r-Θ) image of the vessel at the point of the image, as shown in FIG. 4. An example of a cross-sectional image 120 is shown in FIG. 5. By "stacking" these images, a longitudinal image 105, i.e., an image along the longitudinal axis, or z axis, of the vessel may be generated, an example of which is also shown in FIG. 5. Such an image is known in the art as a "cut-plane" image. The longitudinal image 105 may be rotated along the z axis to display the image 105 at different angles, Θ, until desired features appear.

Figure 2:
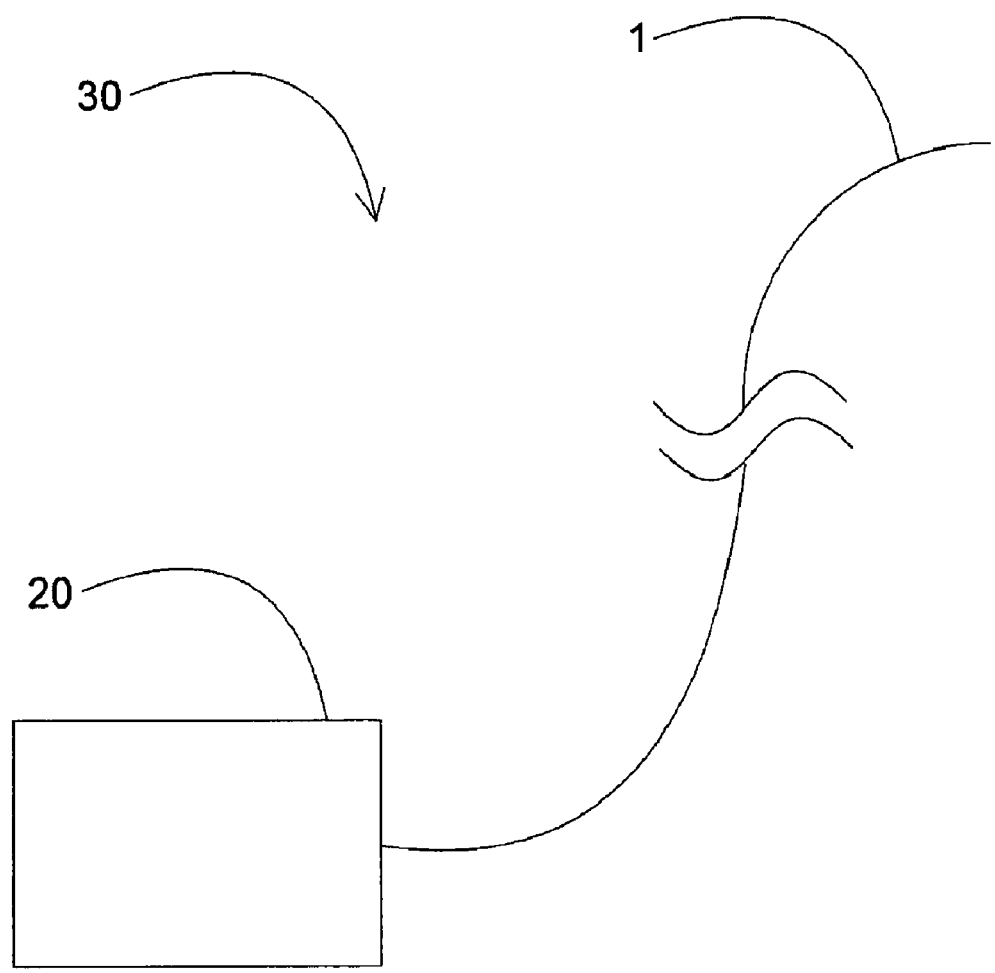
FIG. 2 is a block diagram of a medical imaging system known in the art.
Figure 6:
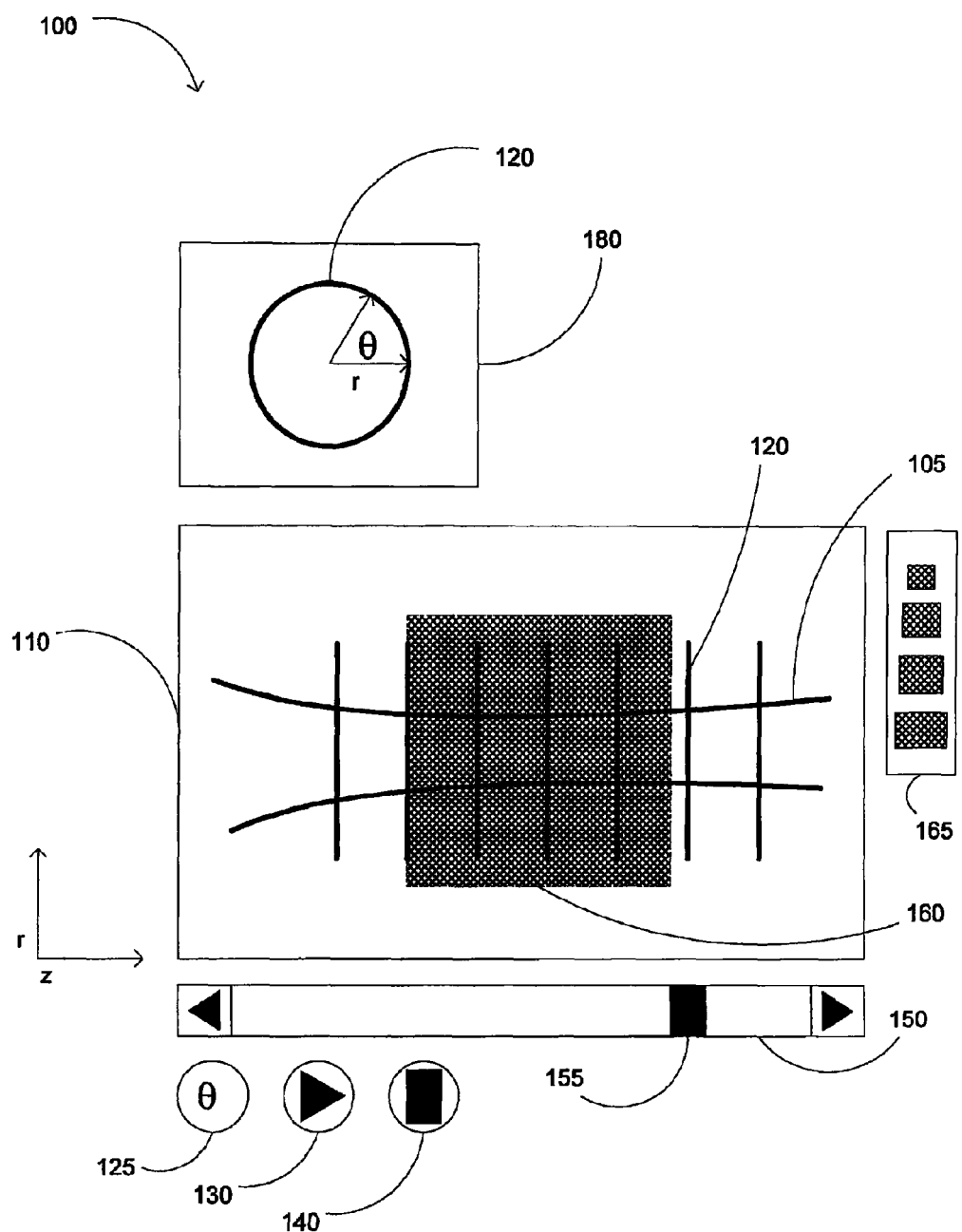
FIG. 6 depicts a user interface for displaying a longitudinal medical image in accordance with a preferred embodiment of the present invention.

The longitudinal image 105 is typically generated by a software program, which may reside within the imaging console 20, shown in FIG. 2. The software program displays the image on a display device (not shown) of the imaging console 20. Turning to FIG. 6, the software program may include a user interface 100. The user interface 100 includes a first window 110, which displays a longitudinal image 105 of a vessel. As mentioned above, the longitudinal image 105 comprises of a plurality of r-Θ cross-sectional images obtained over time as the catheter 21 is being pulled back. Each of these r-Θ images may be regarded as frames 120, and the longitudinal image 105 may be displayed as an animation sequence presenting each frame 120 sequentially. These frames 120 are typically generated at a rate of approximately 30 frames/sec, and the catheter 21 is typically pulled back at a speed of approximately one-half mm/sec. Thus, the frames 120 are typically displayed very close together.

The user interface 100 may include control elements that allow a user to control the display of the longitudinal image 105. The control elements may include a playback element 130, a stop playback element 140, and an adjust cut-plane position element 125, which allows a user to rotate the longitudinal image 105 along the z axis. Also included is a frame control 150 element that allows a user to scroll through the frames 120, backwards and forwards, and select the display of a particular frame 120 within the sequence. The position of the user selected frame 120 within the sequence of the animation is known as the cursor position. The frame control 150 element includes a scrollbar button 155 that indicates the cursor position. The user interface 100 also includes a second window 180, which displays the frame 120, or cross-sectional image, corresponding to the cursor position. The control elements may be buttons, keys, sliders, scrollbars, virtual keys on a touch screen, or other user actuatable devices.

Generally, a clinician would analyze the image for abnormalities, and if an abnormality requiring one or more stents were discovered in the image, the clinician would visually estimate the length and position of the proper stent to be applied in the region of the abnormality. One approach to facilitate the estimation is to provide a graphical tool that allows a clinician to apply a graphical representation of a stent 160 over the longitudinal image 105 being analyzed. The clinician may be able to graphically adjust the size of the stent 160 to a desired size. One approach may be to drag a mouse pointer over a corner of the stent to adjust the size; however, stent sizes are typically pre-defined and pre-packaged by stent manufacturers, and thus the variety of different sizes may be limited. In such a case, it may be desirable to provide a graphical palette 165, or a predefined library, of one or more pre-defined stents with their sizes and other characteristics in the user interface 100. Because the library is predefined with the necessary dimensions and characteristics of each stent, the clinician may simply click on or otherwise select the desired stent within the palette 165 and drag the desired stent to a desired position on the longitudinal image 105 to determine if the selected stent is appropriate. One of ordinary skill in the art may appreciate that additional sizes, characteristics, or devices may be added to the palette 165 or library.

After the clinician has established a desired location, or position, on the longitudinal image 105 to place the stent 160, the clinician may place bookmarks in the image to record the desired location (preferably, one bookmark on each end of the location). The bookmarks essentially record the particular frames 120 that define the desired location within the longitudinal image 105. In addition, the graphical representation of the stent 160 may be transparent to maintain the visibility of the structure of the image 105. Providing a clinician a graphical tool to simulate the length and position of a stent within the image 105 facilitates in the selection of the proper stent size and position prior to placing the actual stent, which are costly and permanent implants, within the area of interest.

Figure 7:
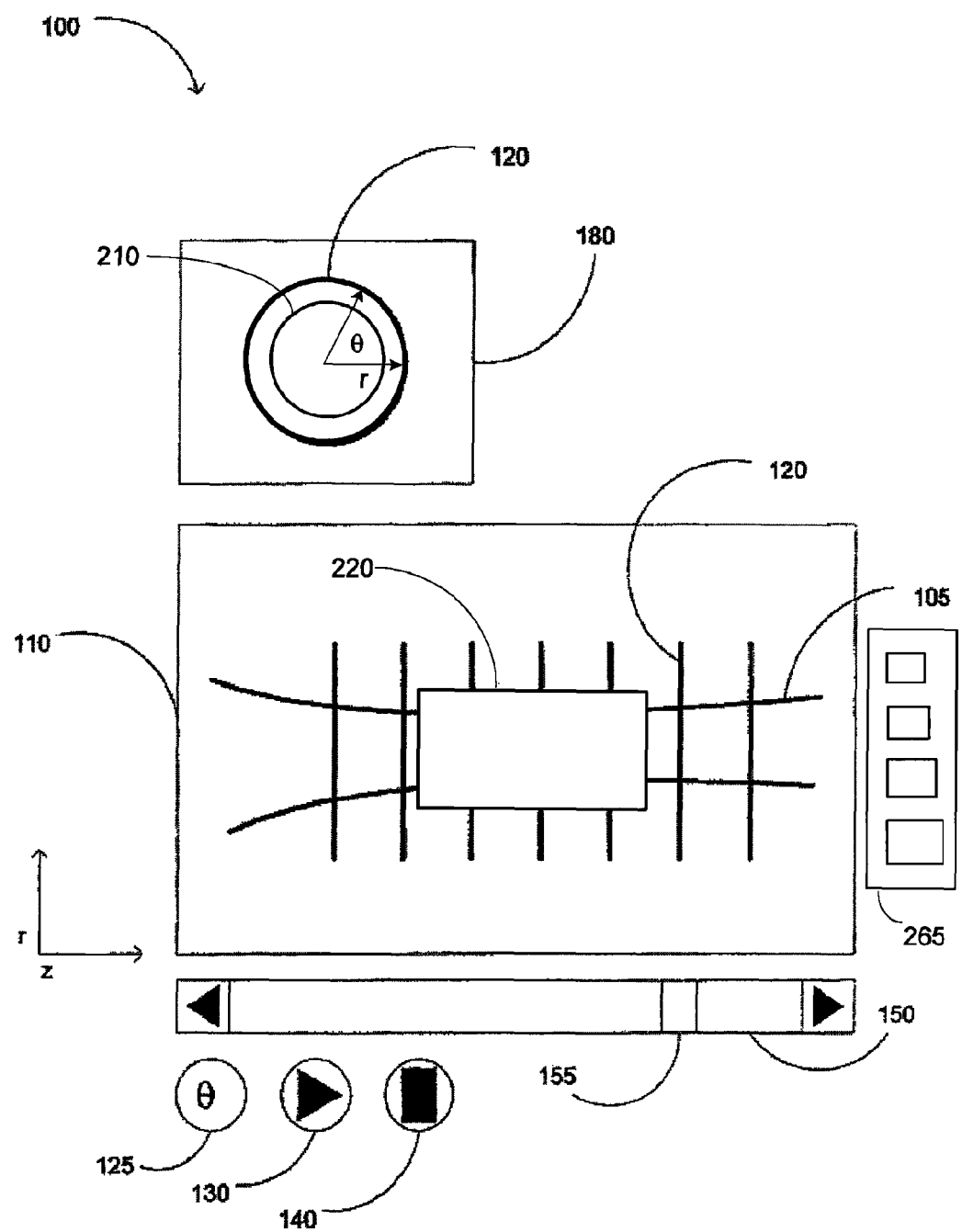
FIG. 7 depicts a user interface in accordance with another embodiment of the present invention.

FIG. 7 shows a user interface 100 with a graphical tool for simulating the dimensions and position of a medical device, e.g., stent, within the patient's body. In this exemplary embodiment, the graphical tool comprises a rectangle 220 overlaid onto the longitudinal image 105 in the first window 110 and a circle 210 overlaid onto the frame 120 in the second window 180. Together, the rectangle 220 and the circle 210 define a cylinder in three-dimensional space with the rectangle 220 representing a longitudinal cross-section of the cylinder corresponding to the longitudinal image 105 and the circle 210 representing a radial cross-section of the cylinder corresponding to the frame 120. In this embodiment, the rectangle 220 and the circle 210 may be used to approximate the size and position of a stent to be applied within the patient's body, in which the stent has a generally cylindrical shape.

In an example, the image 105 and the frame 120 may be images of a blood vessel where the stent is to be applied. In this example, the clinician may move the rectangle 220 within the image 105 and adjust the dimensions of the rectangle 220 to visually approximate the desired position and dimensions of the rectangle 220. The clinician may move the rectangle 220 within the image 105, e.g., by clicking on the rectangle 220 with a mouse or touch pad to select the rectangle 220 and dragging the rectangle 220 to the desired position within the image 105. The clinician may adjust the dimensions of the rectangle 220 by clicking on a boundary of the rectangle 220 to select the boundary and dragging the boundary to adjust one or more dimensions of the rectangle 220. The boundary may darken when selected to visually indicate that the boundary has been selected. For example, the clinician may click on a side boundary of the rectangle 220 and drag the side boundary to adjust the length of the rectangle 220.

In an embodiment, the medical device being applied within the patient's body may only come in pre-defined dimensions. In this embodiment, the clinician may only adjust the dimensions of the rectangle 220 to one of a set of different dimensions corresponding to the pre-defined dimensions of the medical device. In an embodiment, the user interface may include a graphical palette 265 displaying a set of pre-defined rectangles that the clinician can apply to the image 105, where each rectangle corresponds to one of the pre-defined dimensions of the medical device. In this embodiment, the clinician can select one of the rectangles in the graphical palette 265 with the selected rectangle being applied to the image 105.

The clinician may also move the circle 210 within the frame 120 and adjust the dimensions of the circle 210 to visually approximate the desired position and dimensions of the circle 210. The clinician may move the circle 210 within the frame 120, e.g., by clicking on the circle with a mouse or touch pad to select the circle 210 and dragging the circle to the desired position within the frame 120. In this embodiment, movements of the circle 210 within the frame 120 causes corresponding movements of the rectangle 220 within the image 105. For example, moving the circle 210 upward within frame 120 causes the rectangle 220 to correspondingly move upward to track the movements of the circle 210. Similarly, movements of the rectangle 220 within image 105 causes corresponding movements of the circle 210 within the frame 120. The clinician may adjust the radius of the circle 210 by clicking on a boundary of the circle 210 to select the boundary and dragging the boundary to adjust the radius of the circle 210 to a desired radius. The boundary may darken when selected to visually indicate that the boundary has been selected. In this embodiment, changes in the dimensions of the circle 210 within frame 120 causes corresponding changes in the dimensions of the rectangle 220 within the image 105. For example, expanding the radius of the circle 210 within frame 120 causes the height of the rectangle 220 to correspondingly increase. Similarly, changes in the dimensions of the rectangle 220 within image 105 causes corresponding changes in the dimensions of the circle 210 within the frame 120.

Once the dimensions and positions of the circle 210 and the rectangle 220 are chosen, they provide an approximation of the size and position of the medical device to be applied within the patient's body. Although a circle and a rectangle were used in the exemplary embodiment, other shapes may also be used depending on the shape of the medical device to be applied within the patient. Also, different frames 120 may be displayed in the second window 180, e.g., by moving the scrollbar button 155, in which the position of the scrollbar button 155 corresponds to the frame currently displayed in the window 180. In this embodiment, the circle 210 corresponds to the frame 120 currently displayed in the window 180. Displaying different frames 120 in the second window 180 allows the clinician to visualize how the circle 210 fits within different radial cross-sectional images of the patient.

In the foregoing specification, the invention has been described with reference to specific embodiments thereof. It will, however, be evident that various modifications and changes may be made thereto without departing from the broader spirit and scope of the invention. For example, this invention is particularly suited for applications involving stents, but can be applicable for other medical devices. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A medical imaging system comprising:

an elongated tubular member having distal and proximal ends, configured to be inserted into a vessel of a patient;

an imaging device coupled to the distal end of the elongated tubular member and configured to emit one or more energy pulses and receive one or more echo signals; and a console electrically coupled to the imaging device, wherein the console includes a computer-usable medium having a sequence of instructions which when executed by a processor causes the processor to execute a process including generating a longitudinal image of the vessel by stacking cross-sectional frames generated as the imaging device is being pulled back within a vessel, simultaneously displaying the longitudinal image in a first window and one of the cross-sectional frames of the longitudinal image in a second window on a display, generating a user interface comprising a graphical palette, the graphical palette comprising a plurality of longitudinal graphical representations of a medical device generated in at least two different sizes, each of the plurality of longitudinal graphical representations having predefined dimensions, wherein the user interface is configured and arranged to enable a user to select and drag a longitudinal graphical representation of the plurality of longitudinal graphical representations to a selected location in the first window, and wherein when the selected longitudinal graphical representation is dragged to a portion of the first window that includes the cross-sectional frame of the second window a cross-sectional graphical representation of the medical device is overlaid onto the second window.

2. The medical imaging system of claim 1, wherein the imaging device comprises an ultrasound imaging transducer assembly.

3. The medical imaging system of claim 1, wherein the medical device is a stent.

4. The medical imaging system of claim 3, wherein the selected longitudinal graphical representation of the medical device comprises a rectangle and the cross-sectional graphical representation comprises a circle.

5. The medical imaging system of claim 1, wherein the user interface provides controls that allow the user to playback the longitudinal image frame-by-frame.

6. The medical imaging system of claim 1, wherein the distal and proximal ends of a location of the selected longitudinal graphical representation may be bookmarked.

7. The medical imaging system of claim 1, wherein the user interface provides a scroll bar that allows the user to select the frame currently on the display.

8. The medical imaging system of claim 7, wherein the selected longitudinal graphical representation of the medical device comprises a rectangle and the cross-sectional graphical representation comprises a circle.

9. The medical imaging system of claim 1, wherein when the selected longitudinal graphical representation is dragged to the first window, portions of the longitudinal image beneath the selected longitudinal graphical representation are at least partially visible through the selected longitudinal graphical representation.

10. The medical imaging system of claim 1, wherein the user interface is configured and arranged to enable the user to move at least one of the selected longitudinal graphical representation within the first window or the cross-sectional graphical representation within the second window.

11. The medical imaging system of claim 10, wherein movement of the selected longitudinal graphical representation within the first window causes a corresponding movement of the cross-sectional graphical representation within the second window.

12. The medical imaging system of claim 11, wherein movement of the cross-sectional graphical representation within the second window causes a corresponding movement of the selected longitudinal graphical representation within the first window.

13. A method for estimating the size, location, and position of a stent to be applied within a vessel of a patient, comprising the steps of:
generating a longitudinal image of the vessel by stacking cross-sectional frames as an imaging transducer assembly is being pulled back within the vessel;
simultaneously displaying the longitudinal image in a first window and one of the cross-sectional frames of the longitudinal image in a second window on a display; and
generating a user interface comprising a graphical palette, the graphical palette comprising a plurality of longitudinal graphical representations of a medical device generated in at least two different sizes, each of the plurality of longitudinal graphical representations having predefined dimensions, wherein the user interface is configured and arranged to enable a user to select and drag a longitudinal graphical representation of the plurality of longitudinal graphical representations to a selected location in the first window, and wherein when the selected longitudinal graphical representation is dragged to a portion of the first window that includes the cross-sectional frame of the second window a cross-sectional graphical representation of the medical device is overlaid onto the second window.

14. The method of claim 13, wherein the selected longitudinal graphical representation of the medical device comprises a rectangle and the cross-sectional graphical representation comprises a circle.

15. The method of claim 13, wherein the user interface provides controls that allow the user to playback the longitudinal image frame-by-frame.

16. The method of claim 13, wherein a location of the selected longitudinal graphical representation of the medical device relative to the vessel may be established by the user.

17. The method of claim 16, wherein the location may be bookmarked.

18. The method of claim 13, wherein generating a user interface comprises generating a user interface configured and arranged to enable the user to move at least one of the selected longitudinal graphical representation within the first window or the cross-sectional graphical representation within the second window.

19. The method of claim 18, wherein movement of the selected longitudinal graphical representation within the first window causes a corresponding movement of the cross-sectional graphical representation within the second window.

20. The method of claim 18, wherein movement of the cross-sectional graphical representation within the second window causes a corresponding movement of the selected longitudinal graphical representation within the first window.

21. A system for estimating the size, location, and position of a stent to be applied within a vessel of a patient, comprising:
a means for generating longitudinal image of the vessel by stacking cross-sectional frames as an imaging transducer assembly is being pulled back within the vessel;
a means for simultaneously displaying the longitudinal image in a first window and one of the cross-sectional frames of the longitudinal image in a second window on a display; and
a means for generating a user interface comprising a graphical palette, the graphical palette comprising a plurality of longitudinal graphical representations of a medical device generated in at least two different sizes, each of the plurality of longitudinal graphical representations having predefined dimensions, wherein the user interface is configured and arranged to enable a user to select and drag a longitudinal graphical representation of the plurality of longitudinal graphical representations to a selected location in the first window, and wherein when the selected longitudinal graphical representation is dragged to a portion of the first window that includes the cross-sectional frame of the second window a cross-sectional graphical representation of the medical device is overlaid onto the second window.

22. The system of claim 21, wherein the selected longitudinal graphical representation of the medical device comprises a rectangle and the cross-sectional graphical representation comprises a circle.

23. The system of claim 21, wherein the user interface provides controls that allow the user to playback the longitudinal image frame-by-frame.

24. The system of claim 21, wherein a location of the selected longitudinal graphical representation of the medical device relative to the vessel may be established by the user.

25. The system of claim 24, wherein the location may be bookmarked.

26. The system of claim 21, wherein the user interface is configured and arranged to enable the user to move at least one of the selected longitudinal graphical representation within the first window or the cross-sectional graphical representation within the second window.

27. The system of claim 26, wherein movement of the selected longitudinal graphical representation within the first window causes a corresponding movement of the cross-sectional graphical representation within the second window.

28. The system of claim 26, wherein movement of the cross-sectional graphical representation within the second window causes a corresponding movement of the selected longitudinal graphical representation within the first window.

29. A non-transitory computer-usable medium having a sequence of instructions stored thereon which, when executed by a processor, causes said processor to execute a process for estimating the size, location, and position of a medical device to be applied within a vessel of a patient, the sequence of instructions comprising:

generating a longitudinal image of the vessel by stacking cross-sectional frames as an imaging transducer assembly is being pulled back within the vessel;

simultaneously displaying the longitudinal image in a first window and one of the cross-sectional frames of the longitudinal image in a second window on a display; and generating a user interface comprising a graphical palette, the graphical palette comprising a plurality of longitudinal graphical representations of a medical device generated in at least two different sizes, each of the plurality of longitudinal graphical representations having predefined dimensions, wherein the user interface is configured and arranged to enable a user to select and drag a longitudinal graphical representation of the plurality of longitudinal graphical representations to a selected location in the first window, and wherein when the selected longitudinal graphical representation is dragged to a portion of the first window that includes the cross-sectional frame of the second window a cross-sectional graphical representation of the medical device is overlaid onto the second window.

* * * * *